United States Patent
Mathonnet (10) Patent No.: US 8,512,325 B2
(45) Date of Patent: Aug. 20, 2013

(54) FREQUENCY SHIFTING MULTI MODE ULTRASONIC DISSECTOR

(75) Inventor: Olivier Mathonnet, Chassieu (FR)

(73) Assignee: Covidien LP, Mansfield, MA (US)

( * ) Notice: Subject to any disclaimer, the term of this patent is extended or adjusted under 35 U.S.C. 154(b) by 771 days.

(21) Appl. No.: 12/713,266

(22) Filed: Feb. 26, 2010

(65) Prior Publication Data

US 2011/0213397 A1    Sep. 1, 2011

(51) Int. Cl.
*A61B 18/04*    (2006.01)

(52) U.S. Cl.
USPC ............................................ 606/27

(58) Field of Classification Search
USPC .................. 606/27, 34, 41, 169; 604/22
See application file for complete search history.

(56) References Cited

U.S. PATENT DOCUMENTS

| | | | |
|---|---|---|---|
| 3,990,452 A * | 11/1976 | Murry et al. | 606/169 |
| 4,428,748 A * | 1/1984 | Peyman et al. | 604/22 |
| 4,698,058 A * | 10/1987 | Greenfeld et al. | 604/266 |
| 5,026,387 A * | 6/1991 | Thomas | 606/169 |
| 5,255,669 A * | 10/1993 | Kubota et al. | 601/3 |
| 5,454,809 A | 10/1995 | Janssen | |
| 5,628,743 A | 5/1997 | Cimino | |
| 6,027,515 A | 2/2000 | Cimino | |
| 6,055,458 A | 4/2000 | Cochran et al. | |
| 6,216,704 B1 | 4/2001 | Ingle et al. | |
| 6,246,912 B1 | 6/2001 | Sluijter et al. | |
| 6,425,912 B1 | 7/2002 | Knowlton | |
| 6,471,659 B2 | 10/2002 | Eggers et al. | |
| 6,575,969 B1 | 6/2003 | Rittman, III et al. | |
| 6,585,664 B2 | 7/2003 | Burdorff et al. | |
| 6,622,731 B2 | 9/2003 | Daniel et al. | |
| 6,652,514 B2 * | 11/2003 | Ellman et al. | 606/37 |
| 6,749,624 B2 | 6/2004 | Knowlton | |
| 7,077,820 B1 * | 7/2006 | Kadziauskas et al. | 604/22 |
| 7,108,696 B2 | 9/2006 | Daniel et al. | |
| 7,169,146 B2 | 1/2007 | Truckai et al. | |
| 7,278,991 B2 | 10/2007 | Morris et al. | |
| 7,422,586 B2 | 9/2008 | Morris et al. | |
| 7,525,398 B2 | 4/2009 | Nishimura et al. | |

(Continued)

FOREIGN PATENT DOCUMENTS

| | | |
|---|---|---|
| EP | 1 070 518 A2 | 5/2000 |
| WO | WO 90/07303 | 7/1990 |
| WO | WO 2004/052182 A2 | 6/2004 |

*Primary Examiner* — Michael Peffley
*Assistant Examiner* — Daniel Fowler (57) ABSTRACT

An ultrasonic surgical dissection system and method that employs an ultrasonic waveform that provides improved dissection of tissue while simultaneously providing improved hemostasis is disclosed. The disclosed system provides an ultrasonic waveform that includes a carrier frequency that may be pulse modulated at a predetermined rate and/or duty cycle. Embodiments are presented wherein the disclosed system provides an ultrasonic waveform having a frequency modulated carrier frequency. Additionally or alternatively, the disclosed waveform may be amplitude modulated. In yet another embodiment, an amplitude modulation of the ultrasonic signal may be synchronized, at least in part, with a frequency modulation of the ultrasonic signal. The frequency modulation and/or amplitude modulation may include continuously variable modulations and/or substantially instantaneous transitions between a first frequency and a second frequency and/or a first amplitude and a second amplitude.

8 Claims, 6 Drawing Sheets

(56) References Cited

U.S. PATENT DOCUMENTS

| | | |
|---|---|---|
| 2002/0120261 A1 | 8/2002 | Morris et al. |
| 2002/0165529 A1* | 11/2002 | Danek .......................... 606/28 |
| 2003/0216732 A1 | 11/2003 | Truckai et al. |
| 2005/0043726 A1* | 2/2005 | McHale et al. ................ 606/27 |
| 2005/0137662 A1 | 6/2005 | Morris et al. |
| 2006/0106375 A1 | 5/2006 | Werneth et al. |
| 2006/0142753 A1 | 6/2006 | Francischelli et al. |
| 2007/0066971 A1 | 3/2007 | Podhajsky |
| 2008/0188878 A1* | 8/2008 | Young .......................... 606/169 |

* cited by examiner

FREQUENCY SHIFTING MULTI MODE ULTRASONIC DISSECTOR

BACKGROUND

1. Technical Field

The present disclosure relates to systems and methods for providing energy to biological tissue and, more particularly, to an ultrasonic dissection system having frequency shifting and multifrequency operating modes, and methods of use therefor.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Ultrasonic energy may be delivered to tissue using a surgical probe that includes a transducer coupled with an end effector, and configured to deliver ultrasonic energy to tissue.

The use of ultrasonic energy in surgical procedures is known to those skilled in the art to be a valuable resource for cutting and fragmenting tissue of a patient. Most of these apparatus incorporate a sinusoidal driving signal which causes the mechanical tip to vibrate at a selected frequency, usually in the range of 20 KHz to 60 KHz.

The benefits associated with the use of ultrasonic energy powered devices, and in particular, ultrasonic instruments for surgical use, are known. For example, the use of an ultrasonic generator in conjunction with a surgical scalpel facilitates faster and easier cutting of organic tissue while accelerating coagulation. Improved cutting may result from increased body tissue-to-scalpel contact caused by the high frequency of vibration of the scalpel blade in relation to body tissue. Improved coagulation may result from heat generated by contact between the high frequency vibrations of a scalpel blade and body tissue.

Ultrasonic instruments may include a variety of end effectors (e.g., cutting blades, shears, hook, ball, forceps, etc.) adapted for specific medical procedures. The ultrasonic end effector is disposed at a distal end of the ultrasonic instrument. These ultrasonic instruments are primarily used in a variety of medical procedures including open surgical procedures, luminal procedures and endoscopic procedures.

It is known that at the lower end of the preferred frequency spectrum, e.g., 20 KHz to 40 KHz, larger tip displacements are possible. It is also known that larger tip displacements provide a better tissue cutting effect than small tip displacements. Ultrasonic energy at the high end of the preferred frequency spectrum, e.g., 40 KHz to 60 KHz, can have a more hemostatic effect. This is due in part to the increased absorption of higher frequency energy by tissue. However, larger tip displacements are not feasible at these higher frequencies. Therefore, devices which operate in this realm may have reduced tissue cutting performance.

SUMMARY

Disclosed is an ultrasonic surgical dissection system and method that employs an ultrasonic waveform that may provide improved dissection (cutting) of tissue and, effectively and concurrently provide improved hemostasis (coagulation). In one embodiment, the disclosed system provides an ultrasonic waveform that includes a carrier frequency which may be pulse-modulated at a predetermined rate and/or duty cycle. In another embodiment, the disclosed system provides an ultrasonic waveform having a frequency-modulated carrier frequency. Additionally or alternatively, the disclosed waveform may be amplitude-modulated. In yet another embodiment, an amplitude modulation of the ultrasonic signal may be synchronized, at least in part, with a frequency modulation of the ultrasonic signal. The frequency modulation and/or amplitude modulation may include continuously variable modulations and/or substantially instantaneous transitions between a first frequency and a second frequency and/or a first amplitude and a second amplitude. The disclosed ultrasonic signal causes corresponding oscillation of at least one ultrasonic transducer included in an ultrasonic surgical instrument, which, in turn, is operably coupled to an end effector, e.g., a scalpel, to cut and/or coagulate tissue. In this manner, waveforms associated with improved dissection and waveforms associated with improved coagulation may be advantageously combined, in an essentially simultaneous manner, to enable a surgeon to effectuate dissection and hemostasis in a single operative step. Additionally, reduced power use may be realized, which may have advantages such as, without limitation, cooler operating temperatures, increased battery life, and reduced maintenance requirements.

In an embodiment, the disclosed ultrasonic surgical system may include a variable frequency oscillator that is configured to generate an oscillator output signal. The oscillator output signal frequency may be determined in accordance with an oscillator control signal provided by a controller. The disclosed ultrasonic surgical system may include a variable gain amplifier having a signal input and a control input. The amplifier signal input is operably coupled to the oscillator output. The amplifier is configured to amplify the oscillator output signal by an amount determined according to an amplifier control signal provided by the controller, to generate an ultrasonic driving signal. The controller is operably coupled to the oscillator and the amplifier, and is configured to provide an oscillator control signal and an amplifier control signal in response to a user input. A user interface operably coupled to the controller is adapted to convey a user input to the controller. An actuator is also operably coupled to the controller and is adapted to convey an actuation signal (to, e.g., activate and deactivate the system to control the delivery of ultrasonic energy to tissue). The disclosed system additionally may include an ultrasonic instrument operably coupled to the amplifier, including at least one transducer adapted to convert the ultrasonic driving signal into ultrasonic energy for application to tissue. The transducer may be configured to selectively generate at least one of longitudinal vibrations, lateral vibrations, or torsional vibrations.

In an embodiment, the disclosed ultrasonic surgical system may include one or more sensors configured to sense an operating parameter of the system, including without limitation a parameter relating to the variable frequency oscillator and/or the variable gain amplifier, and to provide a sensor signal corresponding to the sensed parameter to the controller. The sensor may include a zero-crossing detector.

Also disclosed is a method for generating an ultrasonic surgical waveform, comprising the steps of generating an electromagnetic oscillator signal having a first carrier frequency, and modulating the amplitude of the electromagnetic oscillator signal to generate an electromagnetic driving signal including a plurality of carrier frequency bursts. The resulting electromagnetic driving signal is transduced into an ultrasonic surgical waveform. The disclosed method may further include generating an electromagnetic oscillator signal having a second carrier frequency, wherein successive carrier frequency bursts alternate between the first carrier frequency and the second carrier frequency. Additionally or alternatively, successive carrier frequency bursts may alternate between a first amplitude and a second amplitude.

Further, disclosed is an ultrasonic surgical generator, including a variable frequency oscillator configured to generate an oscillator output signal having a frequency determined according to an oscillator control signal. The ultrasonic surgical generator may include a variable gain amplifier operably coupled to the oscillator, that is configured to amplify the oscillator output signal by an amount determined according to an amplifier control signal, which, in turn generates a driving signal. A controller is operably coupled to the oscillator and the amplifier, and is configured to provide an oscillator control signal and an amplifier control signal in response to a user input. The disclosed ultrasonic surgical generator may additionally include a user interface operably coupled to the controller and adapted to convey a user input to the controller. The generator additionally includes an actuator input, operably coupled to the controller, and adapted to receive an actuation signal from an actuator to convey the actuation signal to the controller. An ultrasonic instrument output is also provided, to deliver the ultrasonic driving signal to an ultrasonic instrument.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings, however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user.

Figure 1:
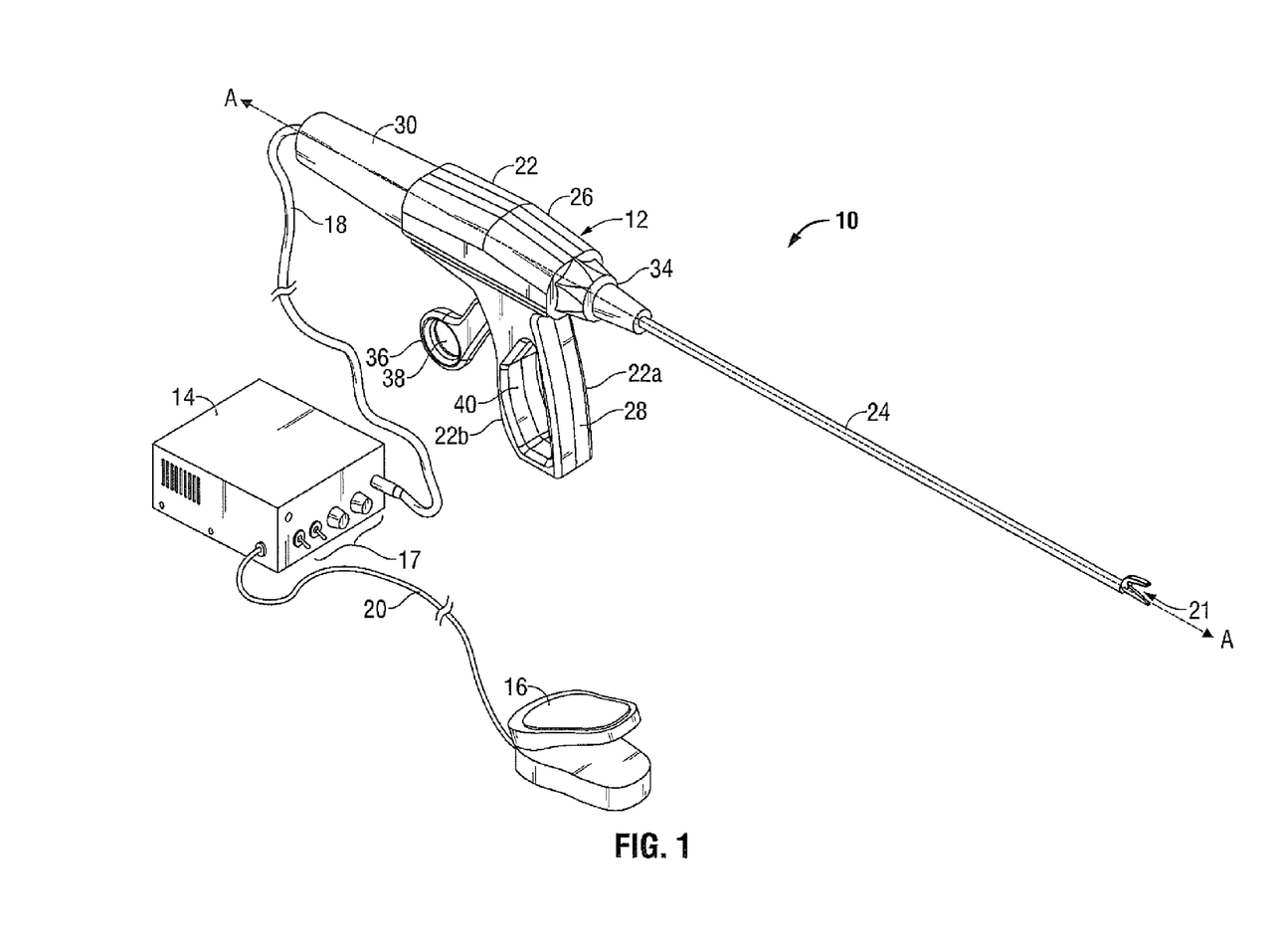
FIG. 1 shows a schematic diagram of an embodiment of an ultrasonic dissection and coagulation system in accordance with the present disclosure.

FIG. 1 illustrates an ultrasonic dissection and coagulation system 10 that includes an ultrasonic instrument 12, an ultrasonic generator module 14, and a remote actuator 16. Ultrasonic generator module 14 is operatively connected to ultrasonic instrument 12 by an electrically conductive cable 18 and functions to control the power and frequency of current supplied to ultrasonic instrument 12. Actuator 16, e.g., a foot switch, is operatively connected to ultrasonic generator module 14 by cable 20. Actuator 16 may be actuated to activate generator module 14, which, in turn, causes an ultrasonic driving signal to be delivered to a transducer 30 of ultrasonic instrument 12. Generator module 14 includes a user interface module 17.

Transducer 30 is operably coupled with ultrasonic end effector 21 of instrument 12 by way of a vibration coupler (contained within barrel portion 26 and body portion 24, not explicitly shown). Transducer 30 converts an ultrasonic driving signal received from generator module 14 into ultrasonic energy (e.g., acoustic or mechanical wave energy), which, in turn, is delivered to end effector 21 to cut and/or coagulate tissue. Transducer 30 may be any suitable transducer capable of converting an ultrasonic driving signal, such as an alternating current electronic signal, into an acoustic or mechanical vibration. By way of example, transducer 30 may include any of a variety of electromechanical conversion elements, e.g., electrodynamic, voice coil, piezoelectric, and/or magnetostrictive elements.

Transducer 30 may include one or more electromechanical conversion elements having distinct ultrasonic characteristics. As an example only, and with respect to a longitudinal axis "A-A" of instrument 12, a first electromechanical conversion element may be adapted to provide a longitudinal wave, a second electromechanical conversion element may be adapted to provide a lateral wave, a third electromechanical conversion element may be adapted to provide a torsional wave, and so forth. One or more electromechanical conversion elements may be selectively activated to enable the generation of longitudinal, lateral, and/or torsional ultrasonic energy, as desired. The disclosed ultrasonic instrument 12 may include one or more transducers 30.

Ultrasonic instrument 12 includes housing 22 and elongated body portion 24 extending distally therefrom. Housing 22 may be formed from molded housing half-sections 22a and 22b and includes a barrel portion 26 having a longitudinal axis aligned with the longitudinal axis of body portion 24, and a stationary handle portion 28 extending obliquely from barrel portion 26. Ultrasonic transducer 30 is supported within and extends from the proximal end of housing 22 and is coupled to ultrasonic generator module 14 via cable 18. Transducer 30 may be a separate component, or incorporated into and/or within ultrasonic instrument 12. Ultrasonic generator module 14 supplies an alternating current electrical signal having an ultrasonic frequency to the transducer 30 to cause oscillation thereof.

The ultrasonic end effector 21 is disposed adjacent the distal end of elongated body portion 24 and is actuated by moving movable handle 36 with respect to stationary handle portion 28. Movable handle 36 and stationary handle portion 28 may include openings 38 and 40, respectively, defined therein that facilitate gripping and actuation of ultrasonic instrument 12. Elongated body portion 24 is supported within rotatable knob 34 and may be selectively rotated by rotating knob 34 with respect to housing 22 to change the orientation of the distal end of ultrasonic instrument 12.

It is to be understood that ultrasonic end effector 21 is an illustrative embodiment of an ultrasonic implement and that other types and/or forms of ultrasonic implements are envisioned, such as a blade, a hook, or a ball, and/or an aspirator assembly. Similarly, it will be appreciated that ultrasonic instrument 12 is an illustrative embodiment of an ultrasonic device and that other instrument forms, e.g., pencil, forceps, scalpel, vessel sealer, and so forth are contemplated within the scope of the present disclosure.

It is to be understood that the ultrasonic dissection and coagulation system 10 and the ultrasonic generator module 14 are provided and explained in detail for example only, and should not be construed as limiting the embodiments of the present disclosure. Indeed, the embodiments disclosed herein may be employed in non-surgical applications including ultrasonic welding, ultrasonic mass flow meters, ultrasonic atomizers or any other suitable electro-mechanical ultrasonic system.

Figure 2:
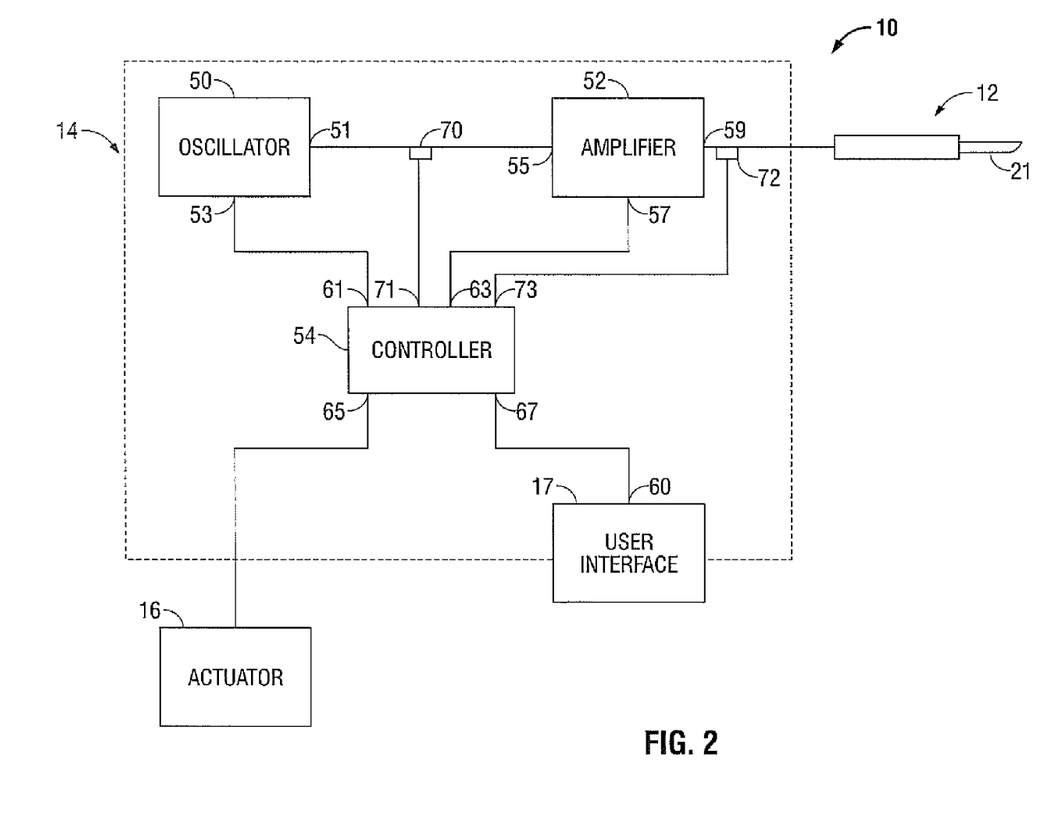
FIG. 2 shows a functional block diagram of an embodiment of an ultrasonic dissection and coagulation system in accordance with the present disclosure.

FIG. 2 is a control block diagram of the disclosed ultrasonic dissection and coagulation system 10 having an ultrasonic generator module 14 that includes (in an operably connected configuration) an oscillator 50, an amplifier 52, a controller 54, and an ultrasonic instrument 12. Oscillator 50 is configured to provide a variable frequency output signal in a range of about 20 KHz to about 60 KHz and includes a signal output 51, and an oscillator control input 53 that is adapted to receive at least one oscillator control signal from controller 54. Oscillator 50 may utilize any suitable manner of ultrasonic signal generation, such as without limitation, a voltage-controlled oscillator (VCO), digitally-controlled oscillator (DCO), digital waveform synthesis, wavetable lookup (e.g., a waveform lookup table with digital to analog conversion), and the like.

Amplifier 52 includes a signal input 55, a driving signal output 59, and an amplifier control input 57. Output 51 of oscillator 50 is operatively coupled to input 55 of amplifier 52. Amplifier 52 is configured to respond to an amplifier control signal received at control input 57 from an amplifier control signal output 63 of controller 54 to adjust an amplifier operating parameter, including without limitation, gain, attenuation, phase, output voltage, output current, output power, and the like. Driving signal output 59 is operatively coupled with ultrasonic instrument 12 to provide an ultrasonic driving signal thereto. Amplifier 52 may utilize any amplification suitable for the dynamic processing of ultrasonic waveforms, including without limitation a voltage-controlled amplifier (VCA), a digitally-controlled amplifier (DCA), class D pulse width modulation, resistor ladder network, and the like.

Ultrasonic dissection and coagulation system 10 includes a controller 54 that is in operable communication with oscillator 50, amplifier 52, actuator 16, and user interface module 17. The communication may be continuous or intermittent. The communicated control data may be communicated in analog form, digital form, using a pulse width modulated signal, using a frequency or analog modulated signal, or any other communication technology. Controller 54 is programmed to at least process data to control the generation of the ultrasonic energy, as described herein. Controller 54 may be embodied in any of hardware, software, software in execution, firmware, microcode, bytecode, in virtualization, in a hardware description language, logic gates, circuitry, digital circuitry, RAM, ROM, MEMS, and the like.

User interface module 17 is configured to receive user input, and provide at least one user interface signal to controller 54. Controller 54 interprets the user input and controls the operation of ultrasonic dissection and coagulation system 10 in accordance therewith. More particularly, controller 54 is configured to control oscillator 50 and amplifier 52 to generate at least one ultrasonic dissection and/or coagulation waveform as described herein. In particular, oscillator 50 generates waveforms in a range of about 20 KHz to about 60 KHz, which may be processed by amplifier 53 to generate one or more ultrasonic dissection and/or coagulation waveforms having various duty cycles, frequencies, peak voltages, peak currents, peak power, and other suitable characteristics.

Controller 54 is further configured to receive at actuator input 65 at least one input from an actuator 16 to selectively control the generation of a desired ultrasonic drive signal. In embodiments, ultrasonic dissection and coagulation system 10 may include two or more actuators 16 that may be coupled to corresponding actuator inputs 65 of controller 54 to enable a user, e.g., a surgeon, to selectively activate ultrasonic dissection and coagulation system 10 in one or more predetermined operating modes.

Controller 54 may include a microprocessor (not explicitly shown) operably connected to a memory (not explicitly shown) which may be volatile type memory (e.g., RAM) and/or non-volatile type memory (e.g., flash media, disk media, etc.). Controller 54 may include any suitable logic processor (e.g., control circuit), hardware, software, firmware, or any other logic control adapted to perform the features discussed herein.

The user interface module 17 may include one or more input controls, such as without limitation, buttons, continuous controls, rotary and/or linear potentiometers, encoders, switches, touch screens, and the like, for controlling at least one operating parameter of ultrasonic dissection and coagulation system 10. Additionally or alternatively, user interface module 17 may include one or more visual indicators and/or display screens (not explicitly shown) for providing the user with variety of output information (e.g., intensity settings, treatment complete indicators, etc.).

The user interface module 17 allows a user (e.g., a surgeon, nurse, or technician) to adjust the ultrasonic energy parameters (e.g., operating mode, output power, waveform, duty cycle, drive voltage, drive current, frequency, and/or other parameters) to achieve the desired ultrasonic energy characteristics suitable to achieve a surgical objective (e.g., dissection, coagulating, tissue sealing, etc.). Additionally or alternatively, user interface module 17 may include a user-selectable desired tissue effect (e.g., hemostasis, coagulation, ablation, dissection, cutting, and/or sealing tissue). Ultrasonic dissection and coagulation system 10 may also include one or more input controls (not explicitly shown) that may be redundant with user interface module 17.

During use, a user, typically a surgeon, may utilize user interface 17 to input one or more operating parameters to controller 54. Actuation of actuator 16 by a use causes controller 54 to communicate one or more control signals to oscillator 50 and/or amplifier 52 which, in turn, causes oscillator 50 and/or amplifier 52 to generate at least one waveform which corresponds to the desired operating parameters. For example, and without limitation, a desired operating parameter may include single frequency mode enable, dual frequency mode enable, a first burst time, a second burst time, a first burst frequency, a second burst frequency, a first burst amplitude, a second burst amplitude, a duty cycle, an on time, an off time, a burst orientation (e.g., longitudinal wave, lateral wave, torsional wave), a burst pattern, and the like. In one embodiment, the disclosed system 10 may include the capability to utilize user interface 17 to store one or more predetermined parameters in a volatile and/or non-volatile memory included within controller 54, which may be selectively recalled for use.

Figure 3:
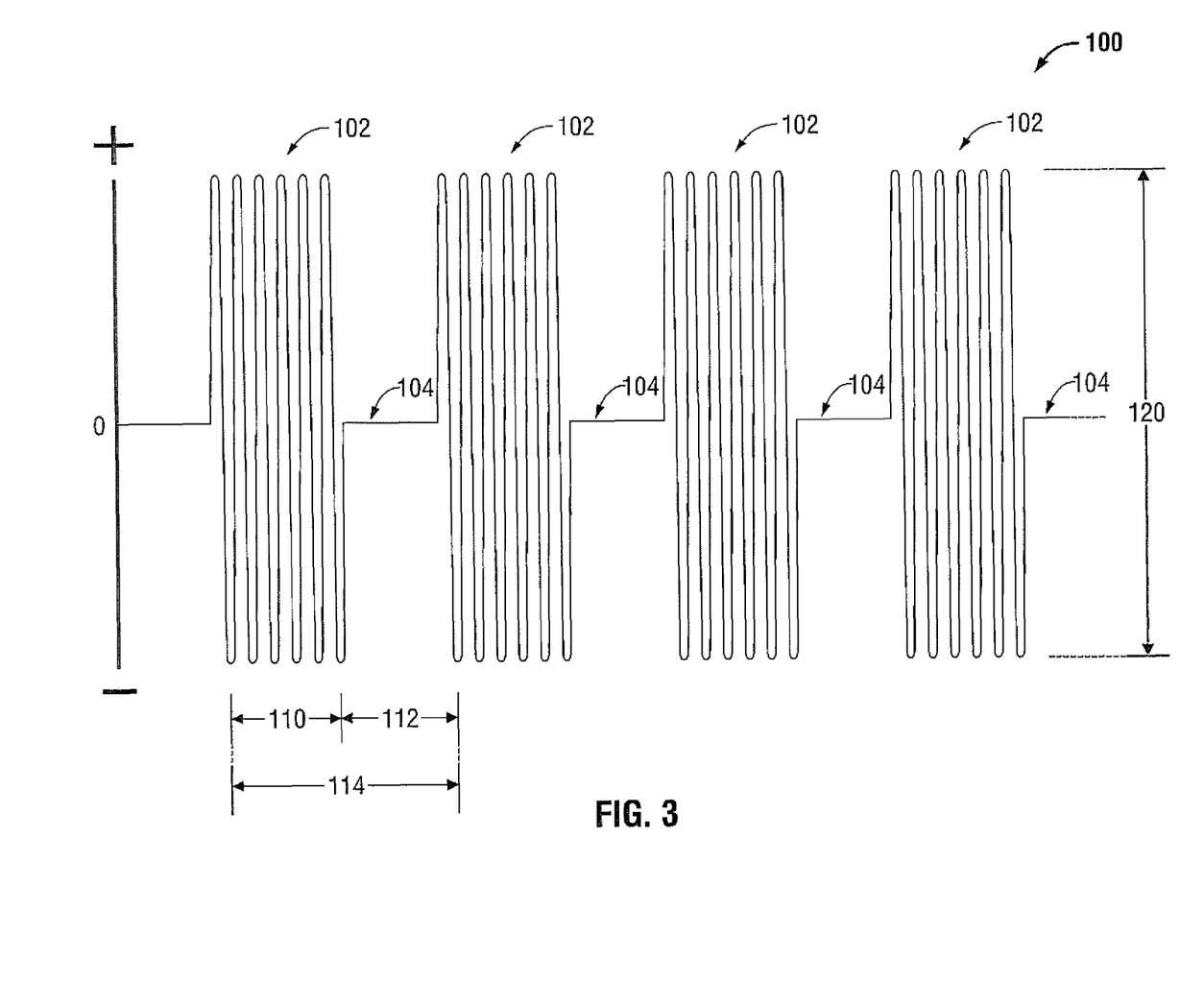
FIG. 3 depicts an ultrasonic waveform generated by an embodiment of an ultrasonic dissection and coagulation system in accordance with the present disclosure.

In one embodiment, the disclosed system 10 may be configured to generate a waveform 100 as shown in FIG. 3. As can be seen, a carrier frequency is amplitude-modulated to form a succession of carrier frequency bursts 102 having an on-time 110, with a null period 104 having an off-time 112 therebetween. The on-time 110 of a carrier frequency burst 102 may be any desired value, e.g., within a range of about fifteen (15) microseconds to about one (1) second, however, it is contemplated that the on-time 110 of a carrier frequency burst 102 may be about twenty (20) milliseconds. The off-time 112 of null period 104 may be any desired value, e.g., within a range of about fifteen (15) microseconds to about one (1) second, however, it is contemplated that the off-time 112 may be about ten (10) milliseconds. Accordingly, a burst repetition interval 114 may be within a range of about thirty (30) microseconds to about two (2) seconds, and may be about thirty (30) milliseconds.

In an embodiment, disclosed system 10 may include at least one sensor 70, 72 that is configured to sense a property of oscillator output 51, amplifier input 55, amplifier output 59, and/or waveform 100, and is operably coupled to controller 54 to provide a waveform property signal thereto. By way of example, the sensor 70, 72 may include a zero-crossing detector adapted to sense a zero crossing of a waveform, and to provide a zero-crossing signal to a sensor input 71, 73 of controller 54. During use, controller 54 may process the zero crossing signal to ensure that a burst 102 begins and/or ends on a zero crossing. In this manner, high frequency transients caused by sharp rising or falling edges, e.g., ringing or glitching, may be minimized or eliminated, which may increase operating efficiency and/or improve cooling of the system 10 and components thereof.

Figure 4:
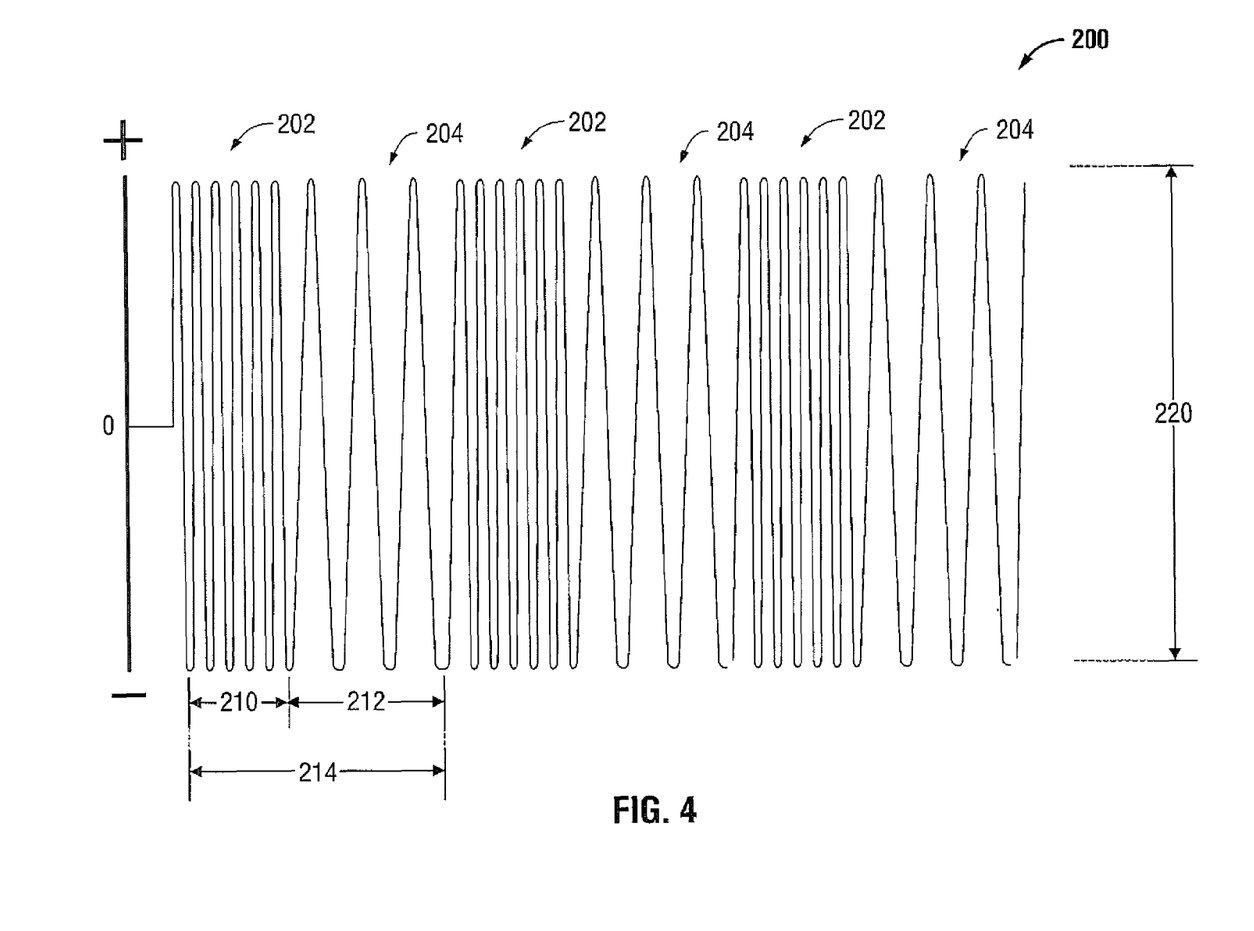
FIG. 4 depicts another ultrasonic waveform generated by an embodiment of an ultrasonic dissection and coagulation system in accordance with the present disclosure.

The system 10 may be configured to generate a waveform 200 as shown in FIG. 4, wherein a carrier frequency is frequency-modulated to form a succession of first carrier frequency bursts 202 and second carrier frequency bursts 204. The first burst time 210 and second burst time 212 may be any desired length of time, e.g., within a range of about fifteen (15) microseconds to about one (1) second, however, it is contemplated that a first burst time 210 and a second burst time 212 may be about twenty (20) milliseconds each, respectively. As shown, a first burst 202 has a higher frequency, e.g., a frequency in a range of about 40 KHz to about 60 KHz, while a second burst 204 has a lower frequency, e.g., a frequency in a range of about 20 KHz to about 40 KHz. In this manner, improved coagulation may be achieved during a first burst 202 while improved cutting may be achieved during a second burst 204. The described frequency modulation may thus provide overall improved cutting and coagulating in an essentially simultaneous manner, which may in turn reduce operative times and improve patient outcomes.

Figure 5:
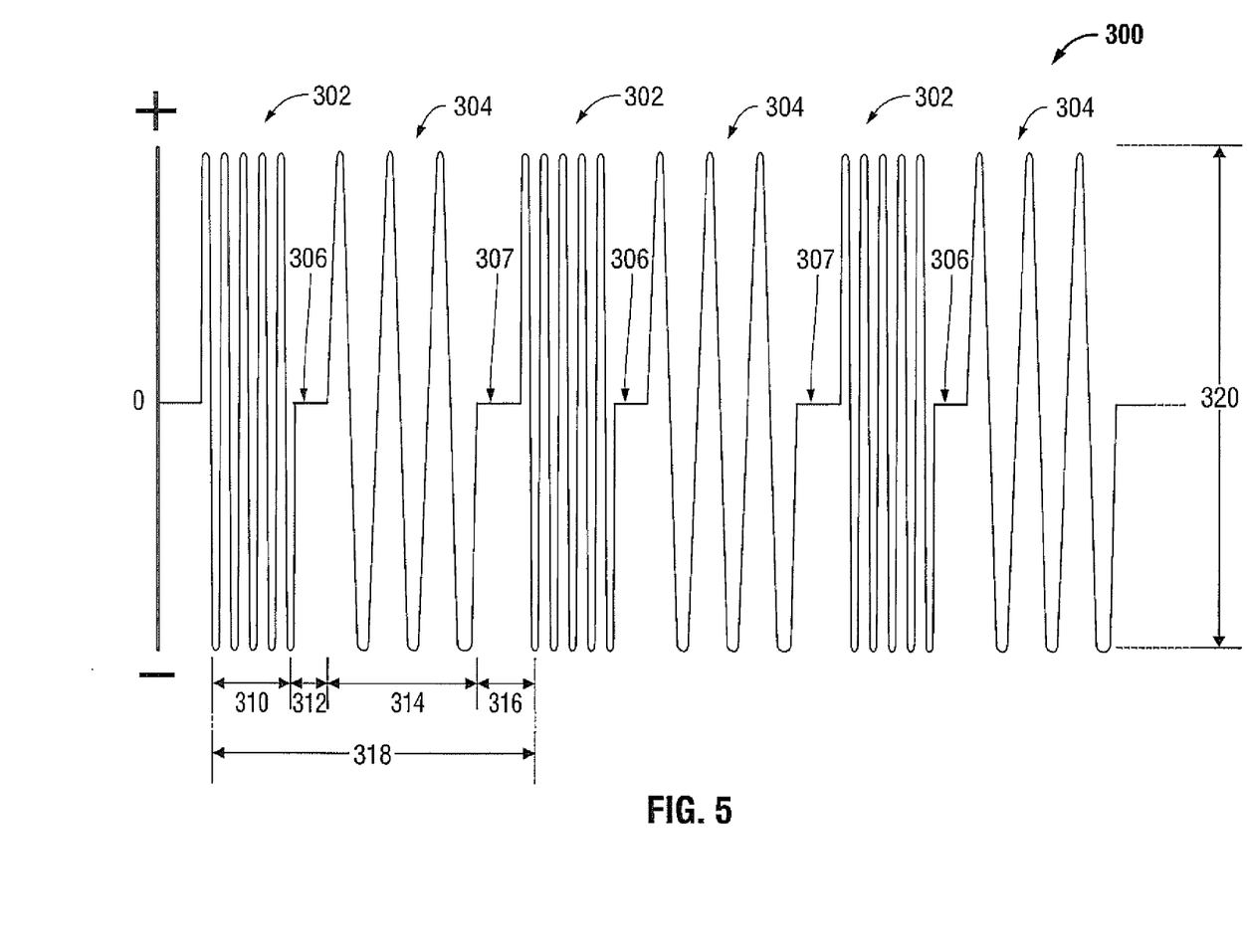
FIG. 5 depicts yet another ultrasonic waveform generated by an embodiment of an ultrasonic dissection and coagulation system in accordance with the present disclosure.

In another variation illustrated in FIG. 5, the system 10 may be configured to generate a waveform 300 wherein a carrier frequency is frequency modulated to form a succession of first carrier frequency bursts 302 and second carrier frequency bursts 304, wherein a first null period 306 having a first off-time 312 follows a first carrier frequency burst 302, and a second null period 307 having a second off-time 316 follows a second carrier frequency burst 304. The first burst time 310 and second burst time 312 may be any desired length of time, e.g., within a range of about 15 microseconds to about one second, however, it is contemplated that a first burst time 310 and a second burst time 312 may be about twenty (20) milliseconds each, respectively. As shown, a first burst 302 has a higher frequency, e.g., a frequency in a range of about 40 KHz to about 60 KHz, while a second burst 304 has a lower frequency, e.g., a frequency in a range of about 20 KHz to about 40 KHz. In this manner, improved coagulation may be achieved during a first burst 302 while improved cutting may be achieved during a second burst 304. Additionally, the first null period 306 and/or the second null period 307 may provide improved cooling of the system 10 and the components thereof, and/or may provide improved temperature control at the operative site which may, in turn, improve patient outcomes.

Controller 54 may utilize a sensor signal provided by the at least one sensor 70, 72 to ensure that a transition from a first frequency to a second frequency, and/or vice versa, occurs at a zero crossing of waveform 300.

Figure 6:
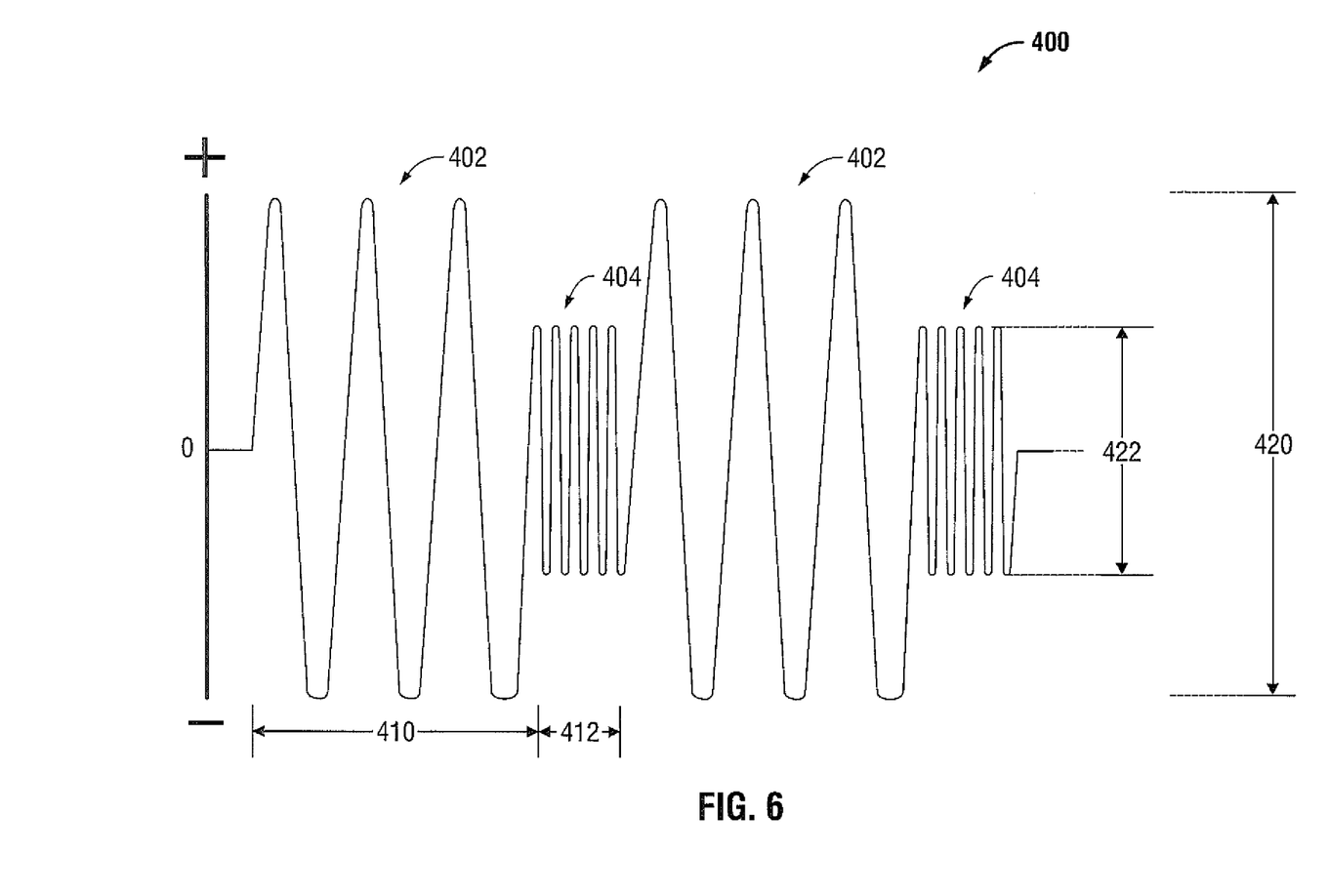
FIG. 6 depicts still another ultrasonic waveform generated by an embodiment of an ultrasonic dissection and coagulation system in accordance with the present disclosure.

In yet another variation illustrated in FIG. 6, the system 10 may be configured to generate a waveform 400 wherein a carrier frequency is frequency-modulated to form a succession of first carrier frequency bursts 402 and second carrier frequency bursts 404. The carrier frequency is additionally amplitude-modulated such that the first carrier frequency burst 402 has a first amplitude 420, and the second carrier frequency burst 404 has a second amplitude 422. As shown, first amplitude 420 may be greater than second amplitude 422, however, it is contemplated that first amplitude 420 may be less than second amplitude 422. The first burst time 410 and second burst time 412 may be any desired length of time as discussed hereinabove, however it is contemplated that a first burst time 410 and a second burst time 412 may be about twenty (20) milliseconds each, respectively. As shown, a first burst 402 has a lower frequency, e.g., a frequency in a range of about 20 KHz to about 40 KHz, while a second burst 404 has a higher frequency, e.g., a frequency in a range of about 40 KHz to about 60 KHz. In this manner, greater larger tip displacements may be achieved during a first burst 402 having a greater amplitude 420, which may provide improved and faster cutting, while, in an essentially simultaneous manner, providing improved control of coagulation during a second burst 404. Additionally or alternatively, an off-time (not explicitly shown) may be provided between first burst 402 and second burst 404, which may provide improved cooling of the system 10 and the components thereof, and/or may provide improved temperature control at the operative site which may, in turn, improve patient outcomes.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. An ultrasonic surgical system, comprising:
a variable frequency oscillator configured to generate an oscillator output signal having a frequency determined according to an oscillator control signal;
a first zero-crossing sensor in operable communication with the oscillator output signal and to generate an oscillator waveform property signal corresponding thereto;
a variable gain amplifier operably coupled to the oscillator and configured to amplify the oscillator output signal by an amount determined according to an amplifier control signal to generate a driving signal;
a second zero-crossing sensor in operable communication with the driving signal and to generate a driving waveform property signal corresponding thereto;
a controller operably coupled to the oscillator, the first zero-crossing sensor, the amplifier, and the second zero-crossing sensor, and configured to provide at least one of an oscillator control signal and an amplifier control signal in response to at least one of the oscillator waveform property signal, the driving waveform property signal, and a user input;

a user interface operably coupled to the controller and adapted to convey user input thereto;

an actuator operably coupled to the controller and adapted to convey an actuation signal thereto; and an ultrasonic instrument operably coupled to the amplifier, including a transducer adapted to convert the driving signal into ultrasonic energy for application to tissue.

2. The ultrasonic surgical system in accordance with claim 1, wherein the controller includes a memory adapted to store a user input.

3. The ultrasonic surgical system in accordance with claim 1, wherein the oscillator output signal has a frequency in a range of about 20 KHz to about 60 KHz.

4. The ultrasonic surgical system in accordance with claim 1, wherein the variable frequency oscillator includes at least one of a voltage-controlled oscillator, a digitally-controlled oscillator, a digital waveform synthesizer, or a waveform lookup table.

5. The ultrasonic surgical system in accordance with claim 1, wherein the variable gain amplifier includes at least one of a voltage-controlled amplifier, a digitally-controlled amplifier, a class D pulse-width modulation amplifier, or a resistor ladder network.

6. The ultrasonic surgical system in accordance with claim 1, wherein the transducer is configured to selectively generate at least one of longitudinal vibrations, lateral vibrations, or torsional vibrations relative to a longitudinal axis of the instrument.

7. The ultrasonic surgical system in accordance with claim 1, wherein the instrument includes two or more transducers that are selectively activatable to generate longitudinal, lateral, or torsional vibrations relative to a longitudinal axis of the instrument.

8. An ultrasonic surgical generator, comprising:

a variable frequency oscillator configured to generate an oscillator output signal having a frequency determined according to an oscillator control signal;

a first zero-crossing sensor in operable communication with the oscillator output signal and to generate an oscillator waveform property signal corresponding thereto;

a variable gain amplifier operably coupled to the oscillator and configured to amplify the oscillator output signal by an amount determined according to an amplifier control signal to generate a driving signal;

a second zero-crossing sensor in operable communication with the driving signal and to generate a driving waveform property signal corresponding thereto;

a controller operably coupled to the oscillator, the first zero-crossing sensor, the amplifier, and the second zero-crossing sensor, and configured to provide at least one of an oscillator control signal and an amplifier control signal in response to at least one of the oscillator waveform property signal, the driving waveform property signal, and a user input;

a user interface operably coupled to the controller and adapted to convey a user input thereto;

an actuator input operably coupled to the controller and adapted to received an actuation signal from an actuator, and to convey the actuation signal to the controller; and an ultrasonic instrument output adapted to deliver the ultrasonic driving signal to an ultrasonic instrument.

* * * * *